(12) United States Patent
Oberli et al.

(10) Patent No.: US 8,618,948 B2
(45) Date of Patent: Dec. 31, 2013

(54) AUTOMATICALLY OPERATING INJECTION DEVICE AND METHOD FOR DETERMINING AN INJECTION OCCLUSION

(75) Inventors: Markus Oberli, Kirchberg (CH); Florian Kuehni, Wabern (CH); Martin Bruegger, Bern (CH); Gilles Prod'hom, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 835 days.

(21) Appl. No.: 12/764,587

(22) Filed: Apr. 21, 2010

(65) Prior Publication Data
US 2010/0245104 A1    Sep. 30, 2010

Related U.S. Application Data

(63) Continuation of application No. PCT/EP2008/008902, filed on Oct. 22, 2008.

(30) Foreign Application Priority Data

Oct. 22, 2007 (EP) .................................. 07405315

(51) Int. Cl.
*G08B 21/00* (2006.01)
(52) U.S. Cl.
USPC .......................................... 340/665; 604/131
(58) Field of Classification Search
USPC .................. 340/665; 604/131, 151, 6, 65, 67
See application file for complete search history.

(56) References Cited

U.S. PATENT DOCUMENTS

| | | | |
|---|---|---|---|
| 5,501,665 A | 3/1996 | Jhuboo et al. | |
| 6,423,035 B1 | 7/2002 | Das et al. | |
| 6,659,980 B2 | 12/2003 | Moberg et al. | |
| 2002/0016569 A1 | 2/2002 | Critchlow et al. | |
| 2004/0133166 A1 | 7/2004 | Moberg et al. | |
| 2007/0191770 A1* | 8/2007 | Moberg et al. ................. | 604/131 |

FOREIGN PATENT DOCUMENTS

| | | |
|---|---|---|
| EP | 1188454 A2 | 3/2002 |
| EP | 1 529 546 A1 | 5/2005 |
| WO | 01/72357 A2 | 10/2001 |
| WO | 2007/093064 A1 | 8/2007 |

OTHER PUBLICATIONS

PCT International Search Report, Appn. No. PCT/EP2008/008902, Filed Oct. 22, 2008, Completion of International Search Feb. 19, 2009, pp. 1-3.
Written Opinion of the ISR, Appn. No. PCT/EP2008/008902, Filed Oct. 22, 2008, pp. 1-5.
Kavanagh, IEEE Transactions on Signal Processing, vol. 49, No. 11, Nov. 2001, pp. 2713-2730.

\* cited by examiner

*Primary Examiner* — Shirley Lu
(74) *Attorney, Agent, or Firm* — Dinsmore & Shohl LLP

(57) ABSTRACT

An automatically operating injection device with an occlusion alarm unit and a method for determining an injection occlusion are disclosed. The method includes generating a plurality of evaluation forces based on a series of force measurements and based on an evaluation time period; determining whether an occlusion exists based on either an evaluation of the plurality of evaluation forces or whether one or more of the series of force measurements exceeds a force threshold; and providing an injection occlusion alarm if an occlusion is determined to exist.

20 Claims, 6 Drawing Sheets

AUTOMATICALLY OPERATING INJECTION DEVICE AND METHOD FOR DETERMINING AN INJECTION OCCLUSION

CROSS REFERENCE TO RELATED APPLICATIONS

This application is a continuation of International Application No. PCT/EP2008/008902, filed Oct. 22, 2008, which claims priority to European Patent application EP 07 405 315.8, filed Oct. 22, 2007.

TECHNICAL FIELD

This disclosure relates to an automatically operating injection device with an occlusion alarm unit and to a method for determining an injection occlusion. The injection unit may be used for automatic injection of a medicament into the body of a patient over a long period of time. It is generally insulin that is injected, although other medicaments to be injected over a long period of time such as, for example, analgesics may be used as well.

BACKGROUND

As background, automatically operating injection devices may inject a predefined volume of a medicament into the body of a patient at predefined time intervals. This volume may be withdrawn from a reservoir, typically a replaceable ampoule, via a pump mechanism and may be injected through an injection needle or catheter placed in the patient's body. If an occlusion is present, the pressure in the injection system may increase, since there is no release of pressure provided by the injections. As a result, a force that is to be applied in the pump mechanism may increase over several unsuccessfully performed injections. A force measurement thus may make it possible to ascertain whether or not there is an occlusion. If an occlusion occurs, the patient may no longer be supplied with a necessary medicament. Moreover, since the pump unit may operate automatically at predefined time intervals, the pressure in the ampoule and in the feed lines to the patient's body may increase, which could cause damage to the injection device. An additional problem is that, with increasing pressure, the occlusion may suddenly dissipate causing the patient to receive too large a quantity of the medicament. By using a measurement unit that determines a force necessary for discharging the medicament, it may be possible to ascertain whether an occlusion is present.

Against this background, embodiments of the present disclosure are capable of quickly determining when an occlusion occurs in an injection device with a higher level of accuracy.

SUMMARY

In one embodiment an injection device for automatically injecting a medicament into a human comprises an injection unit, a measurement unit, a first memory, a second memory, a switching unit, an evaluation unit, and an occlusion alarm unit, wherein: the injection unit is coupleable to the human to deliver automatically a plurality of injections of the medicament into the human, wherein the plurality of injections are each delivered according to an injection time period; the measurement unit is mechanically coupled to the injection unit and measures an injection force, at the injection time period, for each of the plurality of injections; the first memory is electrically coupled to the measurement unit and stores a value of the injection force for each of the plurality of injections measured by the measurement unit, thereby forming a series of force measurements; the switching unit is electrically coupled to the first memory and the second memory such that the switching unit reads the series of force measurements from the first memory, generates a plurality of evaluation forces based on an evaluation time period, and writes the plurality of evaluation forces to the second memory; the evaluation unit is electrically coupled to the second memory and determines whether to provide an occlusion alarm signal either based on an evaluation of the plurality of evaluation forces or if one or more of the series of force measurements exceeds a force threshold; and the occlusion alarm unit which receives the occlusion alarm signal such that the occlusion alarm unit provides an injection occlusion alarm based on the occlusion alarm signal.

In another embodiment, a method for detecting an injection occlusion in an injection device for automatically injecting a medicament into a human comprises: measuring an injection force, at an injection time period, for each of a plurality of injections automatically delivered by the injection device into the human, thereby forming a series of force measurements, wherein the plurality of injections are each delivered according to the injection time period; generating a plurality of evaluation forces based on the series of force measurements and based on an evaluation time period; determining whether an occlusion exists based on either an evaluation of the plurality of evaluation forces or whether one or more of the series of force measurements exceeds a force threshold; and providing an injection occlusion alarm if an occlusion is determined to exist.

In still another embodiment, a computer-readable medium has computer-executable instructions for performing a method for detecting an injection occlusion in an injection device for automatically injecting a medicament into a human, the method comprising: measuring an injection force, at an injection time period, for each of a plurality of injections automatically delivered by the injection device into the human, thereby forming a series of force measurements, wherein the plurality of injections are each delivered according to the injection time period; generating a plurality of evaluation forces based on the series of force measurements and based on an evaluation time period; determining whether an occlusion exists based on either an evaluation of the plurality of evaluation forces or whether one or more of the series of force measurements exceeds a force threshold; and providing an injection occlusion alarm if an occlusion is determined to exist.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structures are indicated with like reference characters and in which:

Figure 1:
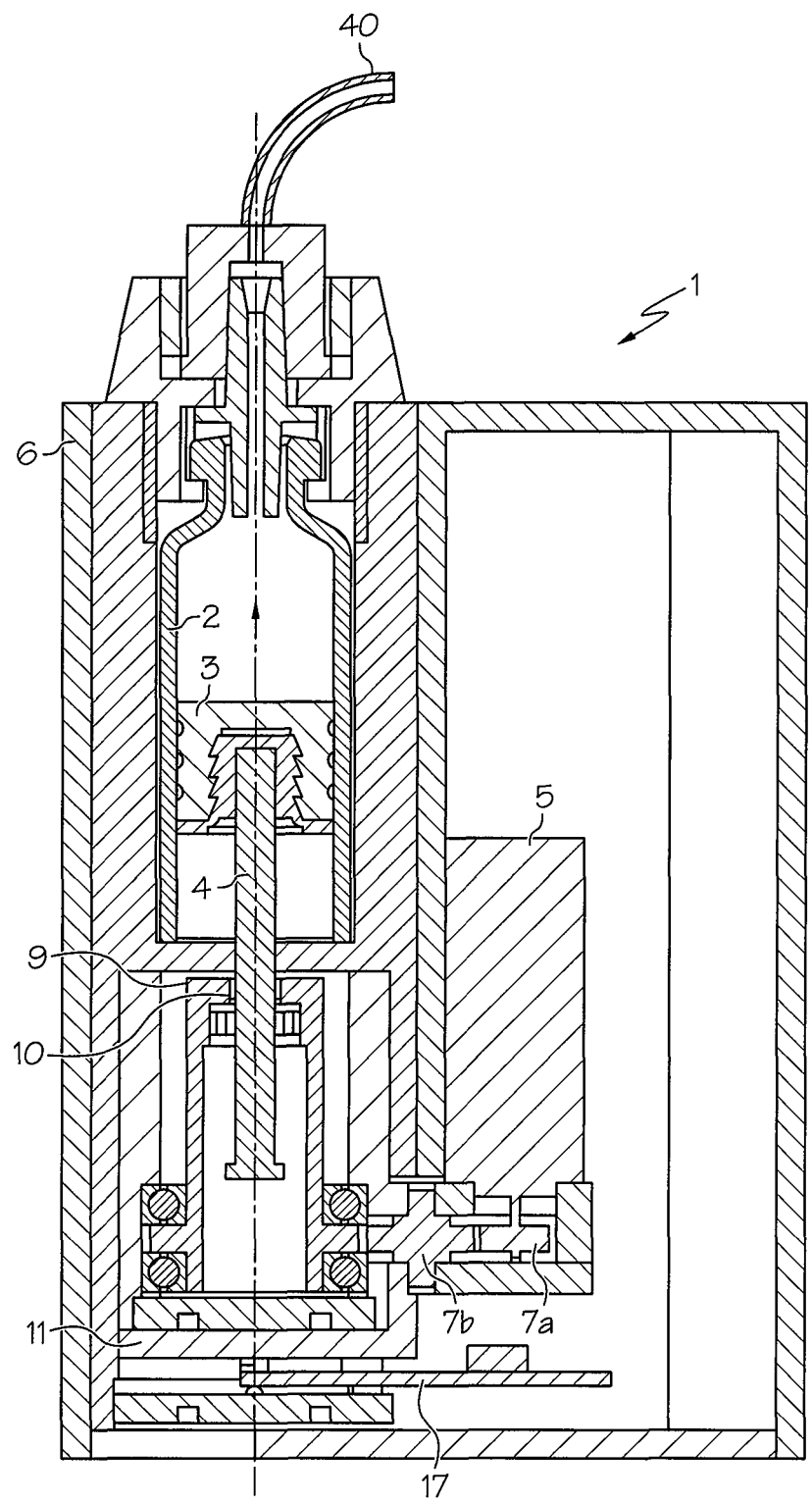
FIG. 1 shows the basic structure of an injection unit according to one or more embodiments shown and described herein.

LIST OF REFERENCE CHARACTERS 1 injection device
2 reservoir
3 piston in 2
4 rod-shaped drive member
5 electric motor
6 housing
7a,b toothed wheels
9 sleeve-shaped drive member
10 thread on 9
11 base
12 alarm unit
13 control unit
16 downsampler
17 force sensor
19 controller for 9
20 1st memory (force values)
21 evaluation unit
23 switching unit
25 2nd memory (diagram and gradient values)
26 comparator unit
27 3rd memory (occlusion force threshold)
29 force increase calculation unit
31 median calculation unit
32 combinational logic unit
33 AND circuit
35 OR circuit
37 diagram
39 1st area (occlusion in 37)
40 catheter
41 2nd area (no occlusion)
43 3rd area (gray area)
44 straight line in 37 (0.5 hour evaluation period)
45 straight line in 37 (1 hour evaluation period)
46 boundary line between 39 and 43
47 boundary line between 41 and 43
49 memory limit value median
100 function block FIX 100
102 FIR coefficient
103 function block FIR 103
104 function block MED 104
105 comparator unit FIR
106 comparator unit MED
107 sequence control
108 element forming differential values
F value of injection force (measured)
D differential value of injection force (measured)

DETAILED DESCRIPTION

Various embodiments of the devices and methods described herein are capable of quickly and accurately determining whether an occlusion exists in an injection device. This may be accomplished by observing and evaluating the injection force measured for each injection. The evaluation time period of the injection force values can be modified by means of a switching unit after a predefined number of injections or after a predefined evaluation period (i.e., the time interval can be lengthened). Such a modification (e.g., lengthening) of the measurement time interval, with simultaneous lengthening of the recording and evaluation period, may result in using force measurements from the previous 8 hours or from the time the device was started, whichever is later. If an occlusion is unambiguously present, the evaluation period can be set to zero and can be re-started after the occlusion has been removed. The modification of the evaluation time period (for the purposes of evaluation) takes place independently of the injection time period between successive injections (e.g., basal release). The injection time period is generally maintained constant, but it could also be modified, for example depending on the time of day. Other time periods are of course possible.

For purposes of this disclosure, "injection time period" is the time period between actual injections of the medicament into the body of the patient. The "evaluation time period" is the time period used by the evaluation unit or comparator unit to evaluate the series of force measurements of the injection device to determine whether an occlusion exists. The evaluation time period is a multiple of the injection time period. For example, if the injection time period was 30 minutes, the evaluation time period can be 30 minutes, 60 minutes, 90 minutes, or any multiple of 30 minutes.

Since, in one embodiment, the injection time period and the evaluation time period are the same, increasing the injection time period also results in an increase in the evaluation time period of the force measurement values. It has been found empirically that longer evaluation time periods permit a more definite conclusion regarding the existence of an occlusion than is possible with shorter evaluation time periods, and false alarms can thus be avoided. Thus, there may be an advantage to having a relatively short injection time period and a relatively long evaluation time period.

The force measurement values can be recorded by a measuring unit as direct force values or as indirectly determined force values. Direct force values will be determined with a force sensor in cooperation with the discharging piston or the drive spindle thereof. In an indirect force measurement unit, for example, a force value concerning a recorded output of the pump mechanism can be determined. A discharged volume of medicament could also be determined. However, a pressure measurement could also be carried out, or drive data concerning a pump motor could be evaluated. In one embodiment, an occlusion evaluation is carried out with a series of force measurement values that are stored for evaluation purposes in a memory.

In order to improve detection of an occlusion, the injection device may comprise (in addition to a first memory for the force measurement values) a second memory which stores increase or gradient values determined statistically from experiments, in particular gradient values of the measured force values, as a function of increasing observation (e.g., evaluation) time periods. The stored gradient values define, in the second memory, a first, a second and a third area. The first area contains values that can be unambiguously interpreted as indicating complete occlusion. The second area contains values that unambiguously indicate no occlusion, and the third area contains values which indicate it is not possible to conclude unambiguously that there is an occlusion or no occlusion. The values to be stored in the second memory are determined statistically from experiments in the laboratory as a diagram, the experiment unambiguously defining an occlusion or no occlusion (e.g. closed or open injection needle).

A comparator unit is provided with which, by comparison with the data stored in the diagram and with the evaluation data, makes it possible to determine whether there is an occlusion, there is no occlusion, or there is no determinable occlusion, depending on where a gradient value (i.e., a force gradient value) determined from several measurement values (force values) over a predefined evaluation time period is located in the diagram. The comparator unit is connected for signaling purposes to the evaluation unit.

To simplify the construction of the injection device and to facilitate the processing of the determined measurement values and gradient values, every nth measurement value stored in the first memory can be selected with the switching unit in the event of an increase in the injection time period between successive measurement values and in the evaluation time period of the measurement values to be processed. It is possible for every second, third, etc., measurement value to be selected. In one embodiment, every second measured force value may be selected. Thus, the force values used for the evaluation can be taken from the series of measured force values, adjusted to the evaluation time period, and re-written to the second memory. This processing of the measurement results permits a simple storage procedure with a shortened recording period, which nevertheless represents an extended evaluation time period. For example, if both the injection time period and the evaluation time period are initially 0.5 hours, the evaluation of the force values can take place after 0.5 hours; if the evaluation time period is doubled to 1 hour, the second evaluation may take place after only one additional 0.5 hours after the first evaluation (for a total evaluation time period of 1 hour).

In addition to the abovementioned evaluation of measurement values over a modifiable evaluation time period, it is possible to have a third memory that stores a force threshold. This fixed value is a safety value which, when met or exceeded by a measurement value during the evaluation period, causes a third occlusion alarm signal to be triggered for the occlusion alarm.

The injection device has a measurement value gradient calculation unit, preferably a force increase calculation unit, which is preferably designed as a FIR filter (Finite-Impulse-Response filter) and with which, from the measurement values of an evaluation period that are stored in the first or second memory, it is possible to determine an increase or gradient value (i.e., an increase of the force value) of the measurement values, which, if it is detectable by the evaluation unit as lying in the first area of the diagram (indicating an occlusion), causes a first occlusion alarm signal.

In addition to the abovementioned gradient calculation unit (or force gradient calculation unit), the injection device can comprise a median calculation unit. With the median calculation unit, differential values determined from two consecutive force values stored in the first or second memory can be sorted in ascending order. In the case of an uneven number of measurement values, there are an even number of differential values. From the sorted differential values, a mean (or average) value can be determined using the two differential values lying in the middle in the sorted differential value series. This mean value can be compared with a stored gradient median threshold, and a second occlusion alarm signal can be generated when this threshold is met or exceeded. If an even number of force measurement values was used, there will be an uneven number of differential values, and the middle value from the sorted differential values can be used for comparison.

For processing the measurement values in a FIR filter for determination of a gradient value (or increase value of the measurement values), an uneven number of measurement values can, in one embodiment, be used to ensure that, as is explained in detail below, adjusting the injection time periods and the evaluation time periods can be done in a simple manner. This uneven number of measurement values can also be used for determination of the median calculation.

The three occlusion alarm signals received above can now each be evaluated individually in order to generate an injection occlusion alarm, although in one embodiment a control unit will be used with a logic AND circuit and a downstream logic OR circuit. The first and second alarm signals are processed with the AND circuit, and this output result and the third alarm signal are combined in the OR circuit. An injection occlusion alarm can be triggered if the OR logic is true. This combinational logic provides additional safety, such that an occlusion that is possibly not detected by the FIR filter still leads to an alarm. This arrangement also significantly reduces the possibility of a false alarm concerning a supposed occlusion.

Further advantageous embodiments and combinations of features will become evident from the following detailed description and from the entirety of the patent claims.

FIG. 1 shows a structural configuration of an injection device 1 according to one embodiment, which may be used for automatically injecting a medicament such as insulin under a patient's skin.

Figure 2:
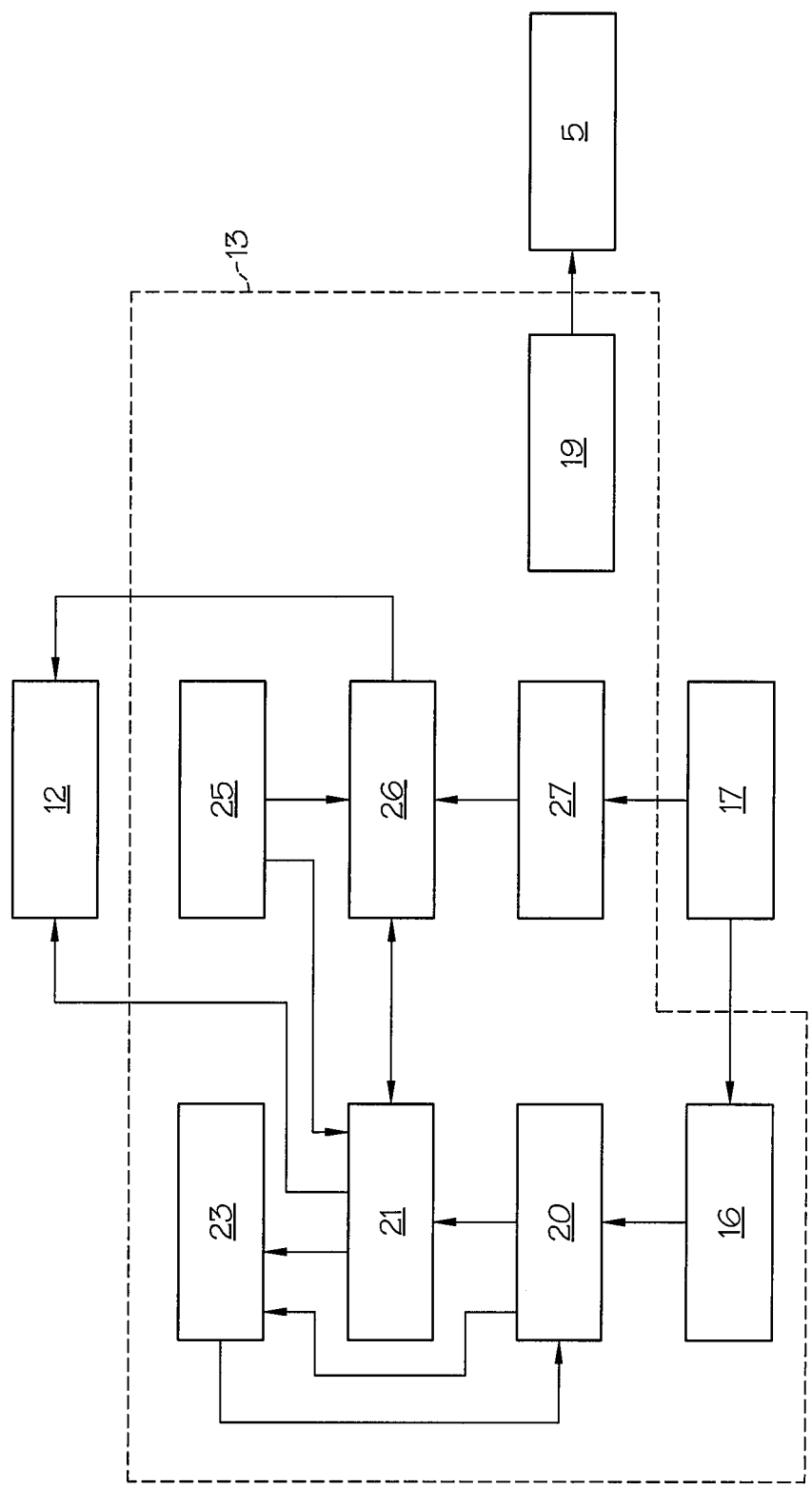
FIG. 2 shows a block diagram of a control unit of the injection unit for occlusion detection, in which intervals for evaluation of measurement values can be modified according to one or more embodiments shown and described herein.
Figure 5:
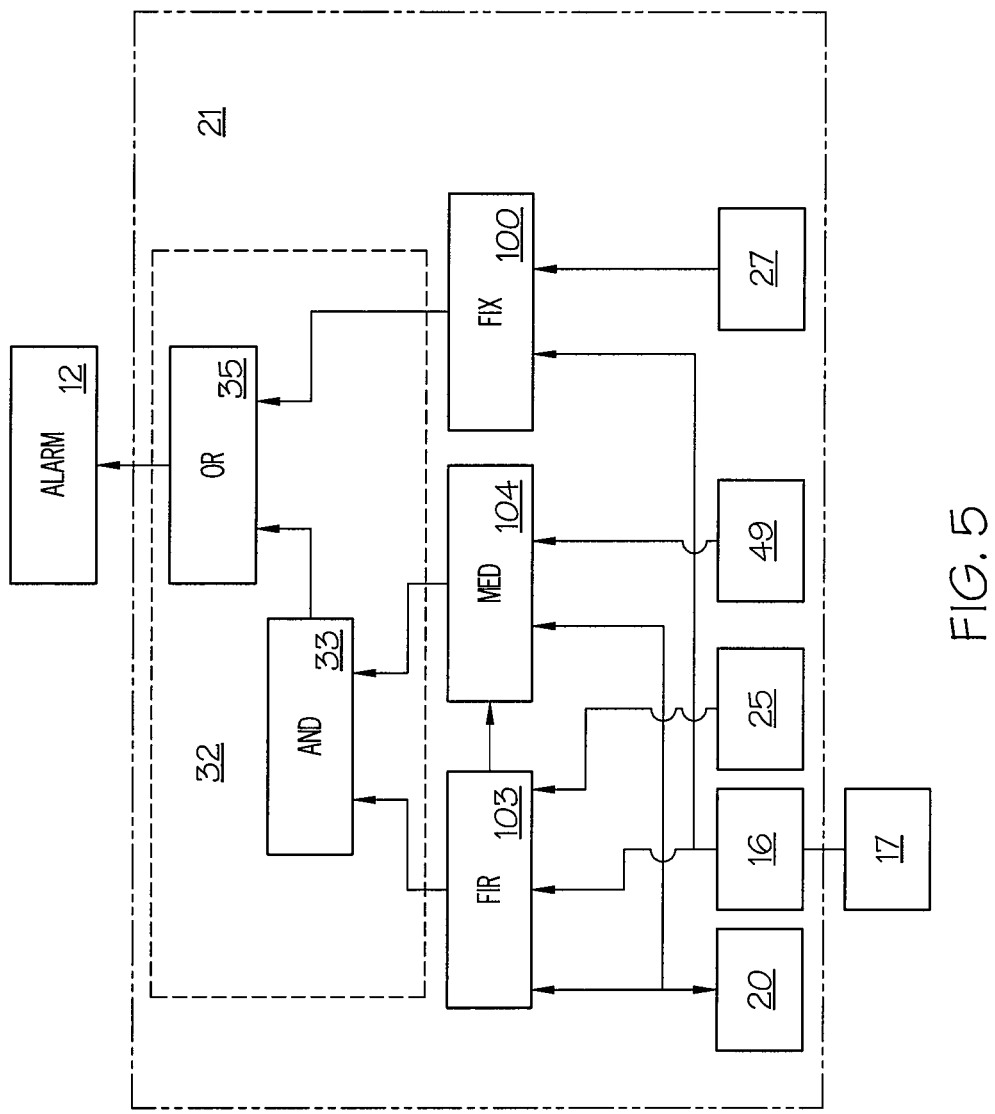
FIG. 5 shows a block diagram in which an occlusion evaluation takes place through combination with a force increase determination, a median calculation, and a fixed threshold evaluation according to one or more embodiments shown and described herein.

The injection device 1 may have a pump mechanism accommodated in a housing 6, a reservoir 2 in which an active substance (e.g., a medicament) is stored, an exchangeable energy supply unit (not shown), an alarm unit 12 shown in FIGS. 2 and 5, and a control unit 13 (shown in FIG. 2) which is used, inter alia, for controlling the pump unit and alarm unit 12.

The pump unit may include a piston 3 which may be disposed in the reservoir 2 and which, via a rod-shaped drive member 4, may be driven by an electric motor 5 and toothed wheels 7a and 7b. The electric motor 5 and force transmission elements—(e.g., toothed wheels 7a and 7b that act on a sleeve-shaped, additional drive member 9 meshing via a thread 10 with the drive member 4) may be arranged on a "free-floating" base 11, which acts on a force sensor 17. The force sensor 17 may be used as a measurement unit for determining, as measurement values, force values F that are to be applied for an injection.

The control unit 13 shown in FIG. 2 comprises, in addition to a controller 19 for the electric motor 5, also a first memory 20 for storing force values F that are detected by the force sensor 17 and transmitted. The control unit 13 moreover comprises an evaluation unit 21 for determining an injection occlusion by processing the force values F stored in the first memory 20. The control unit 13 additionally comprises a switching unit 23 which may be connected to a downsampler 16 and with which, as a function of an evaluation result from the evaluation unit 21, a time interval (e.g., an evaluation time period) between force values F to be stored) may be modified automatically and, in addition, a recording and evaluation period of force values (e.g., force measurements) to be stored and evaluated can be modified automatically. The downsampler 16 may be disposed for signaling purposes between the force sensor 17 and the first memory 20; it may be responsible for the later changing of the interval (e.g., evaluation time period) of measurement values (force values F) to be evaluated. The switching unit 23 is also connected for signaling purposes to the first memory 20 and the evaluation unit 21.

The control unit 13 of the injection device 1 may include a second memory 25 in which, over increasing observation periods, force increase values determined statistically by means of experiments are stored as gradient values in a diagram 37. The control unit 13 may also include a comparator unit 26 which interacts with the evaluation unit 21 and with which, by comparing with the stored data of below-described increase values from diagram 37 determined like a diagram statistically from experiments and with the evaluation data, it is possible to conclude whether there is an occlusion, no occlusion, or no determinable occlusion.

Figure 6:
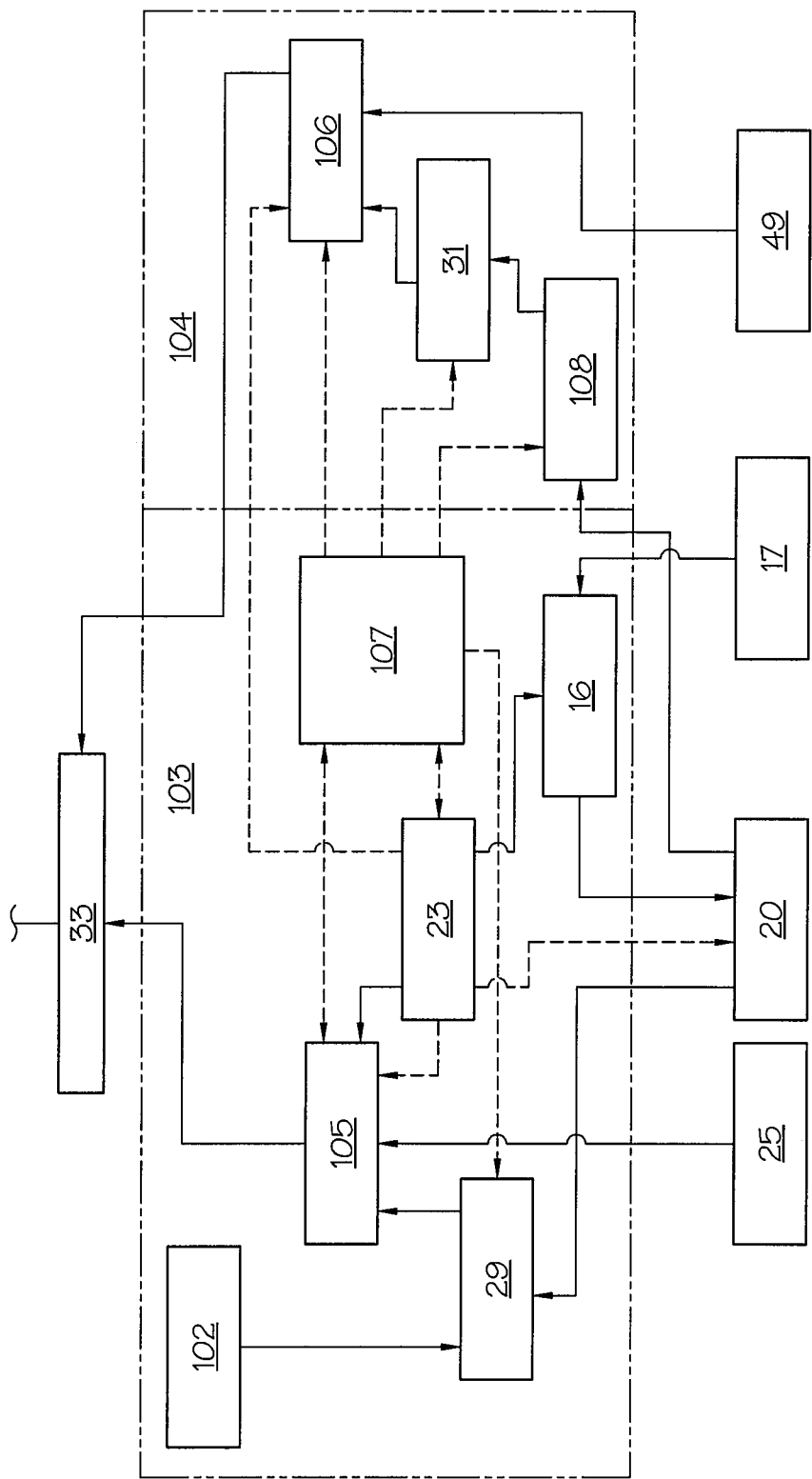
FIG. 6 shows a detailed representation of the function blocks shown in FIG. 5 for FIR filtering and median calculation according to one or more embodiments shown and described herein.

The evaluation unit 21 of the control unit 13 may have a force increase calculation unit 29, shown in FIG. 6, as measurement value gradient calculation unit. In one embodiment, this may be designed as a FIR (Finite Impulse Response) filter and with which, from the force values F of an evaluation period that are stored in the first memory 20 (or second memory 25), a force increase (e.g., force gradient) value can be determined which, if it is detectable by the evaluation unit as lying in the first area, causes a first occlusion alarm signal. The mode of operation of the force increase calculation unit 29 is described in detail below.

In addition to the force increase calculation unit 29, the evaluation unit 21 in one embodiment comprises a median calculation unit 31 with which differential values D, determined from two successive force values F stored in the first memory 20 (or second memory 25), may be sorted in ascending order. A median value can be determined using the two differential values lying in the middle of the sortable differential value series. The median value can be compared with a stored gradient median threshold, and a second occlusion alarm signal can be generated if the median value exceeds this threshold.

The control unit 13 of the injection device 1 may include a third memory 27 for storing a fixed value of an occlusion force threshold which may define an occlusion and which, when exceeded by a force value F in the evaluation period, triggers a third occlusion alarm signal for the injection occlusion alarm. The occlusion force threshold may be a safety value which is intended to avoid pressure being generated that can cause a rupture of the infusion device. In the embodiment described herein, the occlusion force threshold may be set at twenty-five Newtons being exceeded five times in succession.

When using injection force values F, as described here in one embodiment, the method may be based on the exceeding of a threshold. Instead of a threshold being exceeded, however, the measured values may fall below the threshold if, instead of the force values being used as measurement values, use is made of another measurement value such as, for example, a volume that is to be discharged.

The evaluation unit 21 of the control unit 13 may also comprise, in one embodiment, a combinational logic unit 32 described in detail below, with a logic AND circuit 33 for the first and second occlusion alarm signals, and with a logic OR circuit 35 for the output signal of the AND circuit 33 and the third occlusion alarm signal. An occlusion alarm signal can be triggered by the alarm unit 12 if the OR logic is true.

Figure 3:
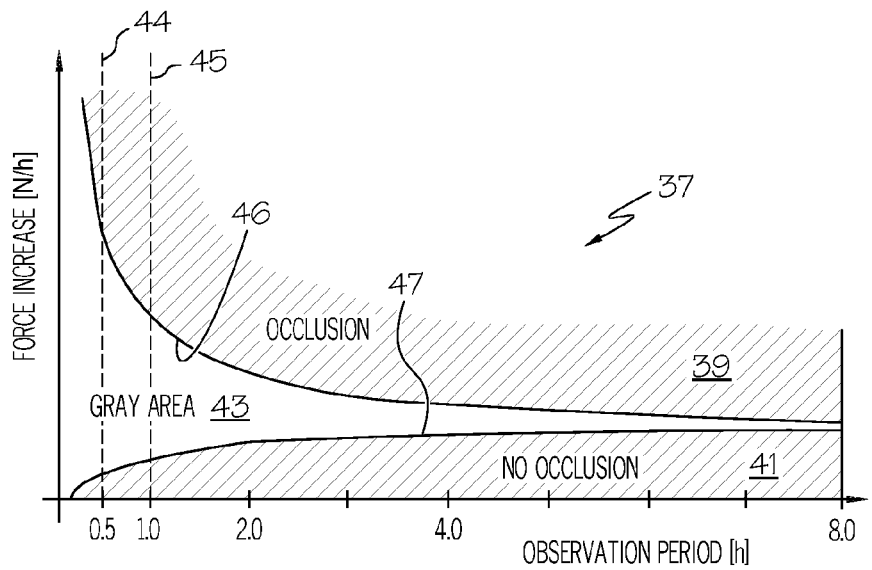
FIG. 3 shows a diagram in which force increase values [N/h] (ordinate) are plotted over an increasing observation period [h] (abscissa) according to one or more embodiments shown and described herein.

The diagram 37 shown in FIG. 3 may be stored in the second memory 25 or other suitable location. The diagram 37 may be integrated into each injection device 1 during its production, i.e. before being supplied to the patient. The diagram 37 may contain force increase (e.g., gradient) values (expressed in Newtons per hour, N/h), plotted over an increasing observation period (hours). The diagram 37 may have been statistically determined beforehand from experiments for each injection device type. The diagram 37 does not have to be set up for each injection device; it only has to be experimentally recorded once per injection device type. The diagram 37 may have a first area 39 in which, experimentally, an occlusion is considered unambiguously present. An occlusion may be easily be produced experimentally by deliberately causing a closure of an injection needle (i.e., catheter) 40 (see FIG. 1) of the injection device 1. A second area 41 of the diagram 37 may clearly define the absence of any occlusion. The absence of an occlusion may also be easily verified experimentally by means of a catheter 40, at whose outer end an injection needle (not shown) is generally arranged, being able to empty freely.

Figure 7:
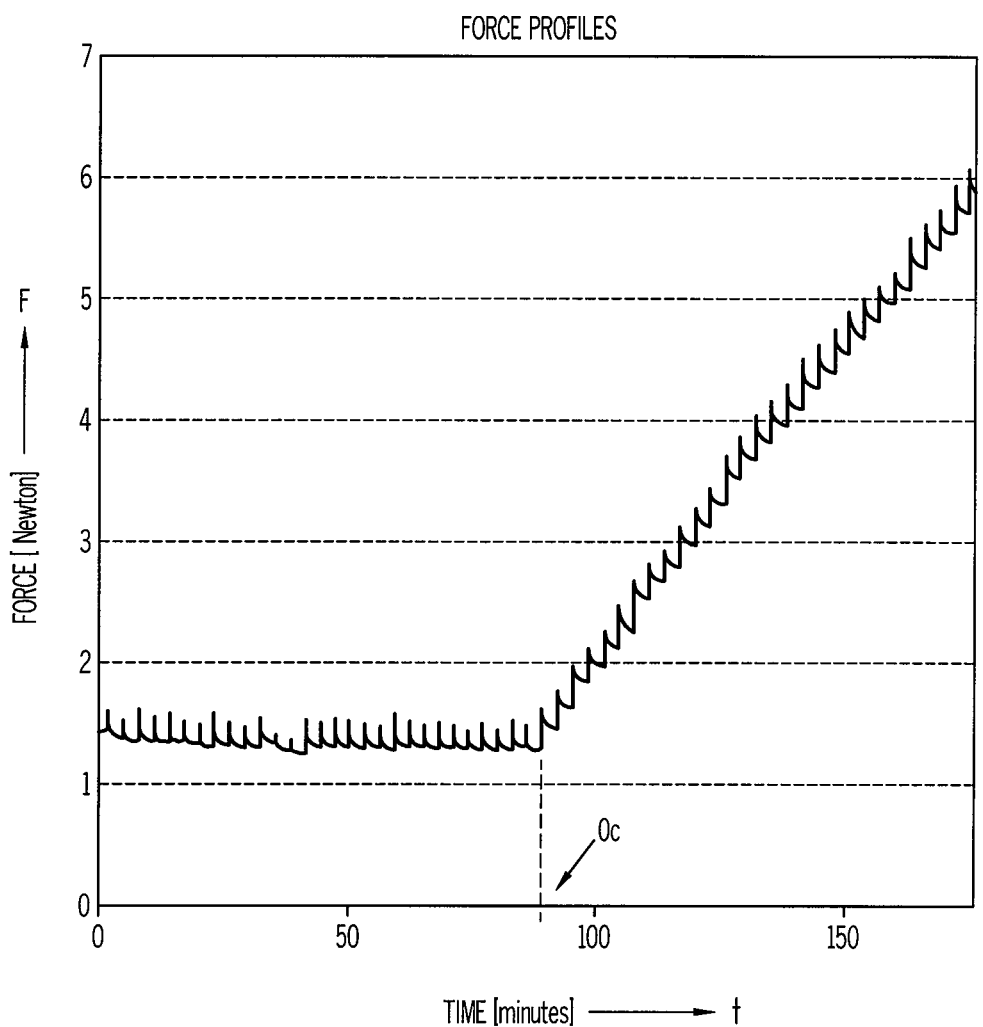
FIG. 7 shows a force profile over time when an occlusion occurs according to one or more embodiments shown and described herein.

In the embodiment discussed hereafter, the measurement values used are force values that are applied for injection of a medicament. FIG. 7 shows a typical force profile in the event of an occlusion occurring at time $O_c$.

The force F to be applied for an injection may be obtained from the following equation $$F = F_0(p) + \epsilon,$$

where function $F_0$ may be a function of the pressure p in the fluid to be injected and may be substantially constant. Variable $\epsilon$ may be a disturbance variable occurring in the injection device which may be desirable to eliminate. Variable $\epsilon$ may depend on the friction of the fluid in the conduits, the piston friction in the reservoir (ampoule), the ambient temperature, electrical disturbances, etc.

If the injection needle is occluded once and then another time not occluded, it is possible to establish, from the values of the force increase calculation unit, data which cannot be assigned either to the first area 39 (unambiguous occlusion) or the second area 41 (no occlusion). That is to say, these results may lie in a third area 43, a gray area. It has ascertained experimentally that, if measurements are carried out over a long observation time period, this third area 43 becomes smaller, and the probability of determining whether or not there is an occlusion becomes increasingly better. It can be determined whether the force gradient lies in the first area 39, the second area 41, or the third area 43 based on setting the observation time period (from the diagram 37) equal to the evaluation time period.

There are several methods for determining a gradient or a force increase over an observation (e.g., evaluation time) period. For example, the following method may be used.

The force values F for each injection may be calibrated in units of Newtons (N), and the measurement may generally be made at a basal release. The measurement may be carried out immediately before the first burst in the respective release interval. In the example shown here, the measurement may be carried out every three minutes. The calibrated force values F may be stored in the first memory 20.

To record the appliance-specific diagram, according to one theory of FIR filtering, 11 force values $F_0$ to $F_{10}$ are determined in a first evaluation cycle, for example, and are stored in first memory 20 (or second memory 25). Of course, an even number of values may also be used. The fewer the measurement values (force values) used, the greater the determination error may be. A large number of values, by contrast, may reduce this error but increases the measurement time. The number of measurement values proposed in one embodiment, namely eleven, has proven optimal, and also an arrangement of the coefficients symmetrical to "0" in the calculation of the gradient by means of FIR filtering. A theory on FIR filtering is described, for example, in IEEE Transactions on Signal Processing, vol. 49, no. 11, November 2001, pages 2713-2730; R. C. Kavanagh "FIR Differentiators for Quantized Signals".

These 11 force values $F_0$ to $F_{10}$ have been recorded at a time interval (e.g., an injection time period) of three minutes between each injection, that is to say in a recording period (or evaluation time period) of thirty minutes.

To determine a force increase over this recording or evaluation time period, T, the individual, chronologically stored force values are now each multiplied by a coefficient $k_0$ to $k_{10}$, where the coefficient values $k_0$ to $k_{10}$ have linearly ascending values between −1 and +1. The coefficients thus may, for example, have the following values:

TABLE 1

| $k_0$ | $k_1$ | $k_2$ | $k_3$ | $k_4$ | $k_5$ | $k_6$ | $k_7$ | $k_8$ | $k_9$ | $k_{10}$ |
|---|---|---|---|---|---|---|---|---|---|---|
| −1 | −0.8 | −0.6 | −0.4 | −0.2 | 0 | 0.2 | 0.4 | 0.6 | 0.8 | 1.0 |

Figure 4:
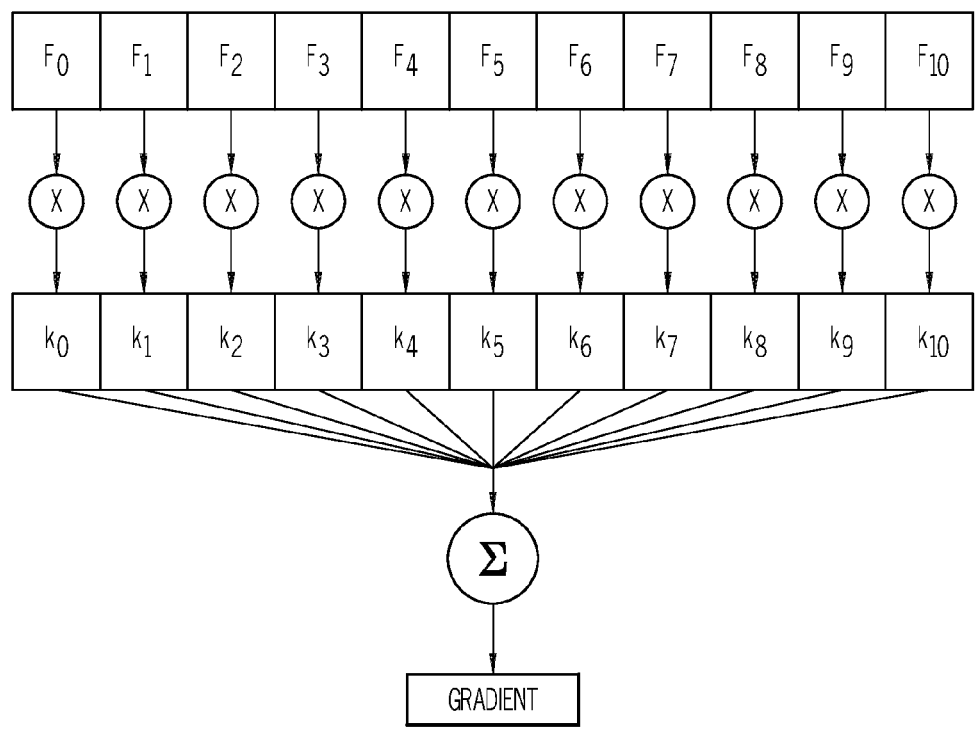
FIG. 4 shows a pictorial representation of the calculation of the force increase according to one or more embodiments shown and described herein.

The oldest value considered thus has the weighting −1, while the newest value is weighted with +1. The multiplication results thus obtained are totaled to determine the force increase:

Force increase (gradient)=$\Sigma(k_i \times F_i)/(T \times \Sigma k_i^2)$ where i=0, 1, . . . , 10 and T is the recording or evaluation time period. FIG. 4 shows the determination of the force increase (gradient).

After this first recording or evaluation time period, an evaluation is carried out in accordance with the above description. The determined increase (gradient) is then compared with the lower gradient limit and the upper gradient limit for that observation time period (e.g., evaluation time period). Three possibilities arise from the comparison result:
1) Occlusion alarm
2) Double recording (e.g., evaluation time) period or
3) Back to initial mode (short measurement time interval)
To double the recording or evaluation time period, every second force value F stored in the first memory 20 is eliminated, after which the remaining force values F are stored in succession (e.g., in the second memory 25). In the further recording or evaluation time period, measurement is carried out with a doubled time interval until a number of measurements corresponding to the preceding recording period is reached:

relatively small after a recording or evaluation period of eight hours. In other words, after this long observation period, a nearly unambiguous conclusion is possible as to whether or not an occlusion has been present.

The type-specific diagram 37 may be stored in the second memory 25 of each injection device 1. When the injection device 1 is started up by the patient or by the physician, then, in the case of a medicament being released every three minutes for example, as explained above, the 11 force values $F_0$ to $F_{10}$ are measured and stored over a period of 30 minutes. The force increase (e.g., gradient) value determined from these 11 force values $F_0$ to $F_{10}$ is compared with values over a corresponding time ordinate value in the stored diagram 37 based on setting the observation time period to the evaluation time period. In FIG. 3, this may be represented by the straight line 44 for a half-hour observation or evaluation time period and the straight line 45 for a one-hour observation or evaluation time period.

If, at the start of a medicament delivery with, for example, a time interval of three minutes between the basal releases, an occlusion is determined after an evaluation period of thirty minutes, with the force increase (e.g., gradient) value then coming to lie in the first area 39, an exceed (i.e., a first occlusion alarm) signal is provided which is forwarded to the combinational logic unit. If an occlusion alarm is triggered according to a method described below, further releases of the medicament are suppressed. If no alarm is triggered, then the procedure is as described below.

If the force increase or gradient value lies in the third area 43 (i.e., in the gray area in which an occlusion cannot be unambiguously determined), then, as has been described above, every second force value stored in the first memory 20 is eliminated by the switching unit 23, and the remaining force values are relocated in succession (e.g., in the second memory 25). New force values are now recorded in succession with a scanning interval that is doubled compared to the first observation or evaluation period. The recording or evaluation period has thus been doubled.

If an occlusion can not unambiguously be determined (i.e., the force gradient lies in the gray area), this procedure may be repeated.

If no occlusion is determined, then the recording or evaluation period is not doubled. However, the value of $F_{10}$ then takes the place of $F_{n0}$ and the remaining force values are eliminated. The operation returns to the starting mode.

TABLE 2

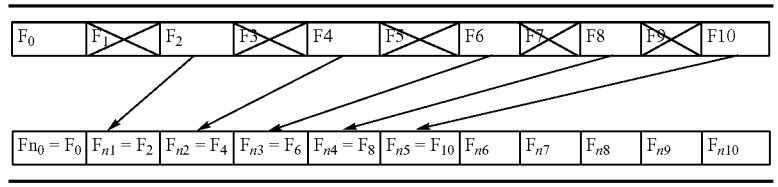

The lower-case "n" in TABLE 2 is intended to signify that this is a new value cycle which, however, also contains previous force values. The relocating shown here can also be performed with another number of force values, but an uneven number of measurements facilitates the relocating procedure.

According to the above algorithm, all extensions of the recording or evaluation period are carried out beginning with a half hour, then one hour, then two hours, four hours, eight hours, and so on. An extension to over eight hours may not be generally necessary, since the gray area has already become It will be noted that, independently of the time intervals (e.g., evaluation time period) for recording the force values F, the time interval (e.g., injection time period) between the basal releases is maintained constant.

Instead of working with force increase or gradient values, it is also possible to work with force values, in which case there is another profile of the boundary lines between the three areas. The boundary lines here come close to straight lines.

In addition to an evaluation of the force increase or gradient to determine an injection occlusion, a median calculation can also be carried out using the values of the injection force from the evaluation time period.

In a first step, the differences of successive force values may be determined:

$$D_0 = F_1 - F_2$$
$$D_1 = F_2 - F_1$$
$$D_2 = F_3 - F_2$$
$$D_3 = F_4 - F_3$$
$$D_4 = F_5 - F_4$$
$$D_5 = F_6 - F_5$$
$$D_6 = F_7 - F_6$$
$$D_7 = F_8 - F_7$$
$$D_8 = F_9 - F_8$$
$$D_9 = F_{10} - F_9$$

The difference values D thus obtained may now be sorted in ascending order, a mean value is formed from the values of D4 and D5, and this mean value is compared with values from a limit value table (e.g., the gradient median threshold). Starting from the diagram 37, the following table shows examples of gradient median threshold values for different observation time periods:

TABLE 3

| | | | | | |
|---|---|---|---|---|---|
| Limit between 1st area 39 and 3rd area 43; line 46 | 8.03 | 7.7 | 7.04 | 5.72 | 4.4 |
| Limit between 2nd area 41 and 3rd area 43; line 47 | 0.275 | 0.55 | 1.1 | 2.2 | 4.4 |
| Limit value "median" (i.e., Gradient median threshold) | 0.06 | 0.06 | 0.06 | 0.10 | 0.20 |
| Observation time period [h] | 0.5 | 1.0 | 2.0 | 4.0 | 8.0 |

The gradient threshold values concerning median calculation may be stored in a memory 49 (see FIG. 5). When evaluating the median values, in contrast to the "force increase or gradient," an unambiguous determination is made between occlusion and no occlusion; there is no gray area here. The gray area may be omitted since, as is explained below, the median values are processed together with the force increase or gradient values determined above. If the median values were to be used alone, which is also possible for detecting an injection occlusion, a gray area can then be defined again and the procedure is analogous to the determination of force increase or gradient values.

Three methods are described above by which an occlusion may be detected. Each of these methods may be used alone. However, it is also possible to combine any two or all three methods. Combining all three methods may permit a reliable determination of an injection occlusion and may reduce false alarms to a minimum. In the case of bolus release, as is customary in insulin patients, the determination using the above-described force increase or gradient calculation could in fact lead to an increased risk of false alarms unless a special software routine was provided for bolus releases caused by the patient.

A combination of the three methods is shown in FIG. 5 in a block diagram with the function block FIX 100 for processing of the occlusion force threshold, the function block MED 104 for the median calculation, and the function block FIR 103 for the FIR filtering. The signal outputs of the blocks FIR 103 and MED 104 are coupled to the inputs of an AND circuit 33. The output of the AND circuit 33 and the output of FIX 100 are coupled to the input of an OR circuit 35. The output of the OR circuit 35 is connected to the alarm unit 12. If the OR condition is fulfilled, an occlusion alarm is triggered.

FIG. 6 shows the two function blocks FIR 103 and MED 104 in a more detailed view than in FIG. 5, the solid lines showing a flow of data and the broken lines showing a control flow.

An input of the AND circuit 33 is connected to a comparator unit 105 of the function block FIR 103. The other input of the AND circuit 33 is connected to the comparator unit 106. A force increase or gradient calculation of the force values may be carried out in the force increase calculation unit 29. A median calculation may be performed by the median calculation unit 31. The differential values for the median calculation are carried out in block 108. The limit values necessary for an evaluation of the median value may be saved in memory 49. All the evaluations and calculations may be controlled by means of the block 107 (sequence control).

The above-described combination of the three evaluation methods "fixed value," "FIR filtering," and "median calculation" may also be carried out without requiring a change of recording or evaluation time period.

If an occlusion alarm has been triggered, the injection device may, in one embodiment, be switched on again only when the injection occlusion has been removed. For this purpose, a first basal release is initiated, and, if the force value measured is greater than 90% of the preceding force value that led to the alarm being triggered, the alarm continues and no further basal release is possible. The determination of the instantaneous force value may, in one embodiment, be combined with the preceding force value based on a time period. The percentage of the force value and the permitted time period are dependent on the characteristics of the injection device.

Force values that increase during an injection occlusion have been discussed above. In an occlusion, however, decreasing measurement values can also be used with other measurement methods. Such a measurement method may be described in International Patent Application Publication No. WO 2007/093064 A1, for example. Decreasing measurement values may be processed analogously to the increasing ones described above.

While particular embodiments and aspects have been illustrated and described herein, various other changes and modifications may be made without departing from the spirit and scope of the disclosure. Moreover, although various inventive aspects have been described herein, such aspects need not be utilized in combination. It is therefore intended that the appended claims cover all such changes and modifications that are within the scope of this disclosure.

What is claimed is:

1. An injection device for automatically injecting a medicament into a human, the injection device comprising an injection unit, a measurement unit, a first memory, a second memory, a switching unit, an evaluation unit, a comparator unit, and an occlusion alarm unit, wherein:
   the injection unit is coupleable to the human to deliver automatically a plurality of injections of the medicament into the human, wherein the plurality of injections are each delivered according to an injection time period;
   the measurement unit is mechanically coupled to the injection unit and measures an injection force, at the injection time period, for each of the plurality of injections;
   the first memory is electrically coupled to the measurement unit and stores a value of the injection force for each of the plurality of injections measured by the measurement unit, thereby forming a series of force measurements;
   the switching unit is electrically coupled to the first memory and the second memory such that the switching unit reads the series of force measurements from the first memory, generates a plurality of evaluation forces based on an evaluation time period, and writes the plurality of evaluation forces to the second memory;

the second memory also stores gradient values of force increase values predetermined statically by experiment as a function over increasing observation periods and which form first, second and third gradient value parts, where the first gradient value part defines a first area in which an occlusion is present, where the second gradient value part defines a second area in which no occlusion is present, and the third gradient value part defines a third area which lies between the first and second areas and in which it is not possible to conclude unambiguously that there is an occlusion;

the evaluation unit is electrically coupled to the second memory and determines whether to provide an occlusion alarm signal based on an evaluation of the plurality of evaluation forces from the comparator unit which concludes that there is an occlusion;

the comparator unit, which is electrically coupled to and interacts with the evaluation unit, is configured to compare the plurality of evaluation forces with the stored gradient values of force increase values predetermined statically by experiment to conclude one of:
that there is an occlusion if the evaluation forces are in the first area defined by the first gradient value part,
that there is no occlusion if the evaluation forces are in the second area defined by the second gradient value part, and
that there is no determinable occlusion if the evaluation forces are in the third area defined by the third gradient value part; and the occlusion alarm unit which receives the occlusion alarm signal such that the occlusion alarm unit provides an injection occlusion alarm based on the occlusion alarm signal.

2. The injection device of claim 1, wherein the evaluation of the evaluation unit, in which to provide the occlusion alarm signal, further includes at least one of a determination that a force gradient for the plurality of evaluation forces exceeds an upper gradient threshold and a determination that a median force gradient for the plurality of evaluation forces exceeds a gradient median threshold.

3. The injection device of claim 2, wherein the evaluation unit determines the force gradient for the plurality of evaluation forces, and the comparator unit generates the occlusion alarm signal based on whether the force gradient exceeds the upper gradient threshold, wherein the upper gradient threshold is based on the evaluation time period.

4. The injection device of claim 2, further comprising a median calculation unit and a second comparator unit, wherein:
the occlusion alarm signal is a first occlusion alarm signal;
the median calculation unit is electrically coupled to the second memory and calculates the median force gradient for the plurality of evaluation forces;
the second comparator unit is electrically coupled to the median calculation unit and generates a second occlusion alarm signal based on whether the median force gradient exceeds the gradient median threshold; and
the occlusion alarm unit is electrically coupled to the second occlusion alarm signal such that the occlusion alarm unit provides the injection occlusion alarm based on a logical "AND" of the first occlusion alarm signal and the second occlusion alarm signal.

5. The injection device of claim 4, further comprising a third comparator unit, wherein:
the third comparator unit is electrically coupled to the first memory and generates a third occlusion alarm signal based on whether one or more of the series of force measurements exceeds the force threshold; and
the occlusion alarm unit is electrically coupled to the third occlusion alarm signal such that the occlusion alarm unit provides the injection occlusion alarm based on a logical "OR" of the third occlusion alarm signal and a result of a logical "AND" of the first occlusion alarm signal and the second occlusion alarm signal.

6. The injection device of claim 1, wherein the evaluation time period is a multiple of the injection time period.

7. The injection device of claim 1, wherein the evaluation time period is 0.5, 1, 2, 4, or 8 hours.

8. The injection device of claim 3, wherein the evaluation unit calculates the force gradient of the plurality of evaluation forces by using a finite-impulse-response (FIR) filter having at least 11 coefficients.

9. The injection device of claim 3, wherein the evaluation time period is based on a previous comparison by the comparator unit, wherein the previous comparison was less than the upper gradient threshold and greater than a lower gradient threshold, wherein the lower gradient threshold is based on the evaluation time period.

10. The injection device of claim 9, wherein the upper gradient threshold and the lower gradient threshold are determined statistically from experiments and are based on an observation time period, wherein:
the force gradient above the upper gradient threshold indicates an injection occlusion;
the force gradient below the lower gradient threshold indicates no injection occlusion; and
the force gradient between the lower gradient threshold and the upper gradient threshold is indeterminate of an injection occlusion.

11. A method for detecting an injection occlusion in an injection device for automatically injecting a medicament into a human, the method comprising:
measuring an injection force with an measurement unit of the injection device mechanically coupled to an injection unit of the injection device which injects the medicament into the human, at an injection time period, for each of a plurality of injections automatically delivered by the injection unit into the human, thereby forming a series of force measurements, wherein the plurality of injections are each delivered according to the injection time period;
generating a plurality of evaluation forces based on the series of force measurements and based on an evaluation time period via a switching unit of the injection device;
determining whether an occlusion exists based on an evaluation of the plurality of evaluation forces being compared by a comparator unit of the injection device to gradient values of force increase values stored as a function over increasing observation periods on the injection device and predetermined statically by experiment in which the gradient values form first, second and third gradient value parts, where the first gradient value part defines a first area in which an occlusion is present, where the second gradient value part defines a second area in which no occlusion is present, and the third gradient value part defines a third area which lies between the first and second areas and in which it is not possible to conclude unambiguously that there is an occlusion, and wherein the comparator unit determines one of:
  that there is an occlusion if the evaluation forces are in the first area defined by the first gradient value part,
  that there is no occlusion if the evaluation forces are in the second area defined by the second gradient value part, and
  that there is no determinable occlusion if the evaluation forces are in the third area defined by the third gradient value part; and
providing an injection occlusion alarm if an occlusion is determined by the comparator unit to exist.

12. The method of claim 11, further comprises determining whether a force gradient for the plurality of evaluation forces exceeds an upper gradient threshold and determining whether a median force gradient for the plurality of evaluation forces exceeds a gradient median threshold.

13. The method of claim 12, wherein the upper gradient threshold is based on the evaluation time period.

14. The method of claim 12, wherein the median force gradient is based on the plurality of evaluation forces.

15. The method of claim 11, wherein the evaluation time period is a multiple of the injection time period.

16. The method of claim 11, wherein the evaluation time period is 0.5, 1, 2, 4, or 8 hours.

17. The method of claim 13, wherein determining whether the force gradient for the plurality of evaluation forces exceeds the upper gradient threshold comprises determining the force gradient by using a finite-impulse-response (FIR) filter having at least 11 coefficients.

18. The method of claim 13, wherein the evaluation time period is based on a previous determination that the force gradient for the plurality of evaluation forces was less than the upper gradient threshold and greater than a lower gradient threshold, wherein the lower gradient threshold is based on the evaluation time period.

19. The method of claim 18, wherein the upper gradient threshold and the lower gradient threshold are determined statistically from experiments and are based on an observation time period, wherein:
  the force gradient above the upper gradient threshold indicates an injection occlusion;
  the force gradient below the lower gradient threshold indicates no injection occlusion; and
  the force gradient between the lower gradient threshold and the upper gradient threshold is indeterminate of an injection occlusion.

20. The injection device of claim 1, further comprising a downsampler connected to the switching unit and configured to modify automatically a time interval between the force values to be stored as a function of an evaluation result from the evaluation unit.

* * * * *

UNITED STATES PATENT AND TRADEMARK OFFICE
CERTIFICATE OF CORRECTION

PATENT NO. : 8,618,948 B2  
APPLICATION NO. : 12/764587  
DATED : December 31, 2013  
INVENTOR(S) : Markus Oberli et al.

Page 1 of 1

It is certified that error appears in the above-identified patent and that said Letters Patent is hereby corrected as shown below:

In the Specification

Col. 11, Line 19, "D4 and D5, and this mean value is compared with values from"  
should read --$D_4$ and $D_5$, and this mean value is compared with values from--;

In the Claims

Col. 13, Claim 1, Line 5, "increase values predetermined statically by experiment"  
should read --increase values predetermined statistically by experiment--;

Col. 13, Claim 1, Line 25, "statically by experiment to conclude one of"  
should read --statistically by experiment to conclude one of--;

Col. 14, Claim 11, Line 43, "measuring an injection force with an measurement unit of"  
should read --measuring an injection force with a measurement unit of--; and Col. 14, Claim 11, Line 60, "device and predetermined statically by experiment in"  
should read --device and predetermined statistically by experiment in--.

Signed and Sealed this  
Twenty-third Day of September, 2014

Michelle K. Lee  
*Deputy Director of the United States Patent and Trademark Office*